(12) United States Patent
Sembritzki et al.

(10) Patent No.: US 6,408,044 B2
(45) Date of Patent: Jun. 18, 2002

(54) METHOD FOR GENERATING A RESULTANT TOMOGRAM FROM A NUMBER OF TOMOGRAMS REGISTERED WITH A COMPUTER TOMOGRAPHY (CT) APPARATUS

(75) Inventors: Otto Sembritzki, Wichenroth; Heinrich Wallschlaeger, Erlangen, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/736,312

(22) Filed: Dec. 15, 2000

(30) Foreign Application Priority Data

Dec. 17, 1999 (DE) .......................................... 199 61 093

(51) Int. Cl.⁷ ................................................ A61B 6/03
(52) U.S. Cl. ............................... 378/15; 378/4; 378/901
(58) Field of Search ............................... 378/4, 15, 901; 382/131

(56) References Cited

U.S. PATENT DOCUMENTS 5,875,225 A    2/1999 Wallschlaeger ............... 378/15
5,946,371 A  * 8/1999 Lai .............................. 378/15

OTHER PUBLICATIONS

"Computer Tomography Scanning with Simultaneous Patient Translation", Crawford et al, Med. Phys., vol. 17, No. 6, Nov./Dec. 1990, pp. 967–982.

* cited by examiner

Primary Examiner—Drew A. Dunn
(74) Attorney, Agent, or Firm—Schiff Hardin & Waite

(57) ABSTRACT

In a method for generating a resultant tomogram from a number of tomograms registered with a computed tomography (CT) apparatus by scanning slices of an examination subject that have different, fixed positions during the scan on a system axis proceeding at a right angle relative to the slices, the attenuation values acquired in the scanning of the individual slices are superimposed to form resulting attenuation values, and the resultant tomogram is reconstructed from the resulting attenuation values.

7 Claims, 2 Drawing Sheets

METHOD FOR GENERATING A RESULTANT TOMOGRAM FROM A NUMBER OF TOMOGRAMS REGISTERED WITH A COMPUTER TOMOGRAPHY (CT) APPARATUS

BACKGROUND OF THE INVENTION

1. Field of the Invention

The present invention is directed to a method for generating a resultant tomogram from a number of tomograms registered with a computed tomography (CT) apparatus by scanning slices of an examination subject that are at different, fixed positions during the scan on a system axis proceeding at a right angle relative to the slices, i.e. what are referred to as transverse slices.

2. Description of the Prior Art

The registration of a sequence of tomograms is a standard technique with great significance in computed tomography. Due to the feed of the examination subject relative to the measuring unit that occurs between the individual tomograms, the individual tomograms are allocated to different z-positions, the z-coordinate indicating the relative position of the slice of the examination subject imaged in the tomogram with respect to the z-direction residing at a right angle relative to the slice plane.

Without further measures, it is not possible to acquire tomograms for z-positions other than those allocated to the registered tomograms. It is also not possible to select the effective slice thickness belonging to the respective nomogram, i.e. the half-width value of the slice sensitivity profile belonging to the tomogram, deviating from the collimated slice thickness this is set by diaphragms, i.e. the expanse in z-direction of the X-ray beam employed for the registration of the tomogram.

Therefore, in known methods of the type initially described, the tomograms are simply calculated from the measured data generated in the scan without influencing the effective slice thickness or the z-position of the individual tomograms. This is considered as disadvantageous in practice for the following reasons:

When subjects, for example organs, or parts thereof project only partially into the slice of the examination subject to be imaged in the respective tomogram, a partial volume artifact arises. It is expressed in a modification of the measured data characterizing the respective subject or subject part and its environment; the contour of the subject or subject part itself also can be changed. Partial volume artifacts become more frequent as the collimated slice thickness becomes larger. Although a reduction of the collimated slice thickness reduces the occurrence of partial volume artifacts, it simultaneously increases the noise amplitude.

If diagnostically relevant regions of an examination subject are to be imaged with different effective slice thicknesses, then a number of sequences with different slice thicknesses must be registered, causing undesirably increased radiation stress for the examination subject.

The measured data acquired during the course of a sequence allow the reconstruction of tomograms only for those z-positions for which tomograms were in fact registered during the sequence. If it turns out later that tomograms of deviating z-positions would be helpful, then these tomograms must be additionally registered, which likewise means an additional radiation stress for the examination subject.

In order to avoid these disadvantages at least to a certain extent, it is known to acquire a resultant tomogram from a number of tomograms of a sequence by forming an average value. For example in that a resultant tomogram having the effective slice thickness nd is calculated from n adjoining tomograms having the collimated slice thickness d. However, the reconstruction time for n individual tomograms is required for the calculation of such a resultant tomogram since these all must be available before the averaging. Such a multiplication of the calculating time is ultimately prohibitive for the described procedure.

German OS 196 25 863 and Crawford et al, "Computed Tomography Scanning With Simultaneous Patient Translation," Med. Phys. 17(6), November/December 1990, pages 967–982, disclose determining the data that belong to a slice exhibiting a specific position on the system axis during the course of the image reconstruction in spiral scanning on the basis of spiral interpolation. The data belonging to the slice to be reconstructed are acquired for the individual projection angles by an interpolation between data that exhibit the respective projection angle but have positions on the system axis that deviate from the position of the slice.

SUMMARY OF THE INVENTION

An object of the present invention is to provide a method of the type initially described that allows the generation of a resultant tomogram without the disadvantage of multiplication of the calculating time.

The above object is achieved in a method for generating a resultant tomogram from a number of tomograms registered with a computed tomography apparatus in accordance with the invention, by scanning slices of an examination subject that have different, fixed positions during the scan along a system axis which proceeds at a right angle relative to the slices. The attenuation values acquired in the scanning of the individual slices are superimposed to form resulting attenuation values and the resultant tomogram is reconstructed from these resulting attenuation values.

The system axis preferably but not necessarily proceeds at a right angle to the planes of the slices.

It is important for the invention that no superimposition of tomograms occurs, but, rather, the generation of the resultant tomogram ensues on the basis of the superimposition of attenuation values belonging to the tomograms to be superimposed to form resultant attenuation values which form the basis from which the resultant tomogram is reconstructed.

The calculating time required for the generation of the resultant tomogram is not significantly longer than the time required for the reconstruction of a single tomogram, since the determination of resultant attenuation values is less time-consuming compared to the reconstruction of a tomogram.

It is advantageous in the inventive method that an influencing of the noise amplitude of the resultant tomogram as well as of the effective slice thickness of the resultant tomogram is possible, namely by modification of at least one of the parameters $N_s$ (number of slices involved in the superimposition), $g(z)$ (weight with which the respective slice contributes to the result of the superimposition) and $\Delta z$ (distance between two successive layers involved in the superimposition).

There is also the possibility of reducing the intensity of partial volume artifacts.

The radiation exposition and the dwell time of the patient in the CT apparatus are reduced in the following applications, that have not been possible with the known procedures for the registration of sequences:

For investigations which require effective layer thicknesses of different sizes (for example, soft tissue and bone diagnostics in the same volume), there is the possibility of implementing bone diagnostics with tomograms that are reconstructed for the collimated slice thickness on the basis of the unmodified attenuation values. Although these have a higher noise amplitude due to the small collimated slice thickness, they are observed with a window width that is far greater than the noise amplitude. Soft tissue diagnostics can then be performed with resultant tomograms that are calculated, with the inventive method according to Equation (3) explained below, for example with $N_s=5$ and $\Delta z=d$, from resultant attenuation values calculated from attenuation values acquired in the course of the same sequence. This procedure is advantageous for the patient because the patient is not exposed to the radiation of a second scan with a larger collimated slice thickness and the patient need not remain in the CT apparatus for the duration of a second scan.

The same advantage is also achieved when effective slice thicknesses of different size are needed in volume regions adjacent to one another. The registration of the attenuation values for the entire volume covering adjacent volume regions can then be implemented in the course of one and the same sequence with a single (small) collimated slice thickness, and a second sequence with a different collimated slice thickness is completely eliminated. The effective slice thickness suitable for the respective volume region is then selected in the reconstruction of resultant tomograms.

DESCRIPTION OF THE PREFERRED EMBODIMENTS

Figure 1:
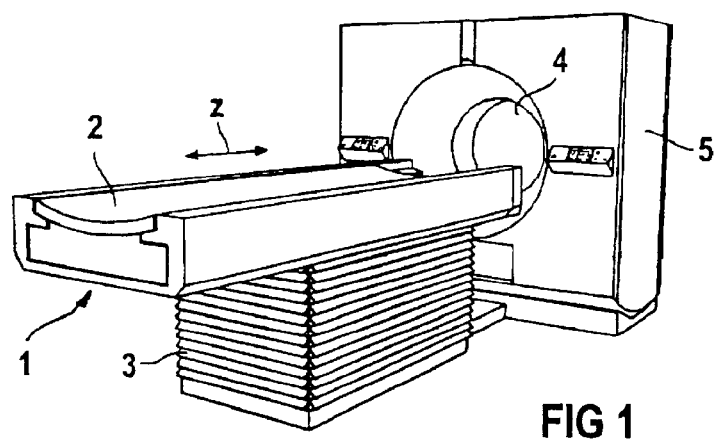
FIG. 1 is a perspective view of an inventive CT apparatus for implementation of the inventive method.

FIG. 1 shows a CT apparatus that has a patient positioning table 1 with a support plate 2 that is displaceable in the direction of the double arrow z in the direction of its longitudinal axis parallel to the system axis of the CT apparatus, the support plate 2 mounted to a base 3 so as to be adjustable in height.

An examination subject lying on the support plate 2, for example a patient 11 (see FIG. 2), can be positioned into the measurement opening 4 of a measuring unit 5 by a corresponding longitudinal displacement of the support plate 2.

Figure 2:
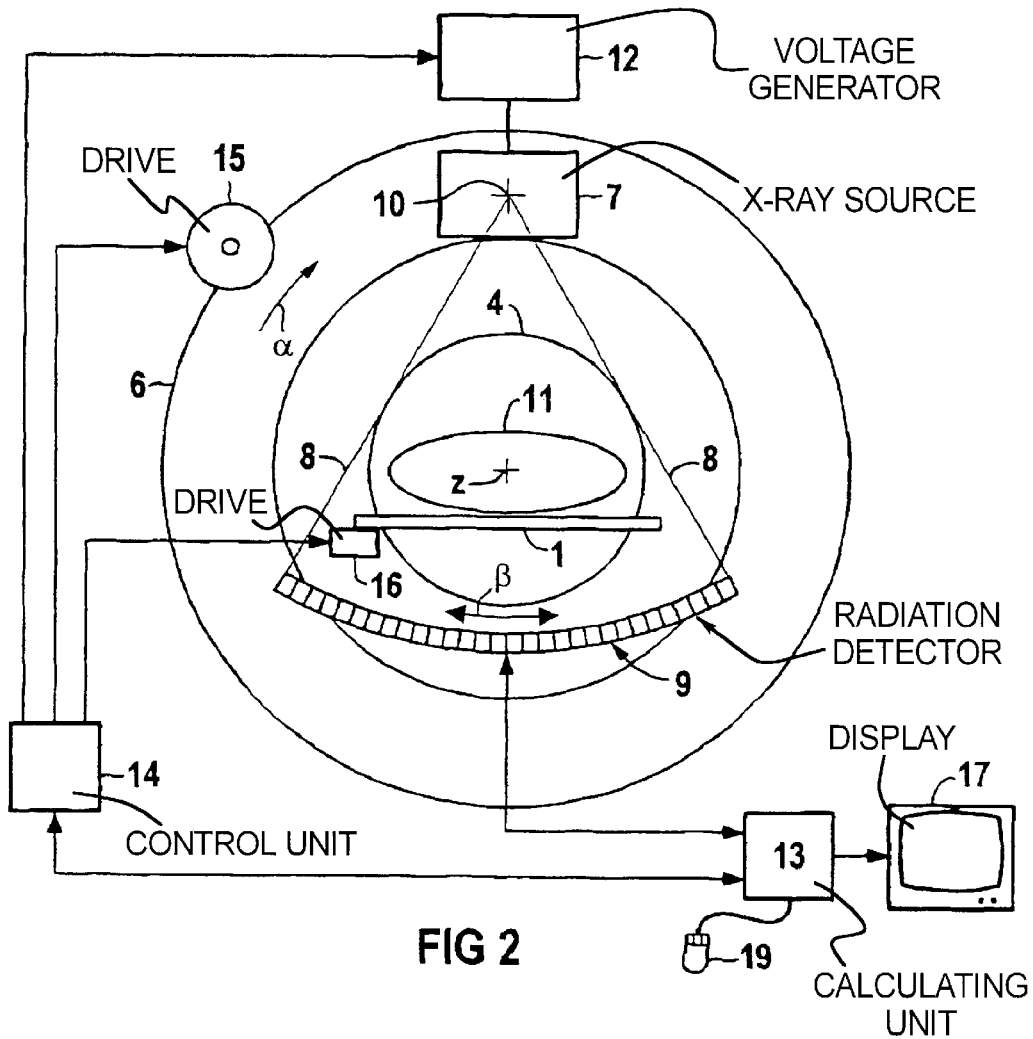
FIG. 2 is a schematic, block circuit diagrammatic illustration of the CT apparatus according to FIG. 1.

As can be seen from FIG. 2, the measuring unit has a live rim 6 surrounding the measurement opening 4 and at which an X-ray source 7 and a detector system 9 are arranged lying opposite one another. The detector system 9 in the exemplary embodiment is formed by an arcuately curved line of, for example, 512 detector elements. A channel angle β is allocated to each detector element.

The X-ray source 7 has a focus 10 from which a fan-shaped X-ray beam 8, incident on the detector system 9, emanates.

A display 17 for the display of tomograms is connected to an electronic calculating unit 13. An input instrument, a mouse 19 in the illustrated exemplary embodiment, is also connected to the electronic calculating unit 13. This input instrument allows the CT apparatus to be operated on the basis of graphic operating menus that can be displayed on the display 17.

A control unit 14, operates drives 15 and 16 respectively allocated to the live rim 6 and to the support plate 2 for controlling the rotary motion of the live rim 6, and the longitudinal motion of the bearing plate 2. The control unit 14 also controls a voltage generator 12 that supplies the X-ray source 7.

For scanning the patient 11 lying on the support plate 2, the live rim 6 is rotated in the α-direction around the system axis z that proceeds centrally through the measurement opening 4 and resides at a right angle relative to the plane of the drawing of FIG. 2. This rotation moves the focus 10 of the X-ray source 7 on a circular path that lies in a plane residing at a right angle relative to the system axis. The fan-shaped X-ray beam 8 emanating from the X-ray source 7, fed by the high-voltage generator 12, transirridiates a planar slice of the patient 11 that proceeds at a right angle relative to the system axis 2.

At predetermined angular positions, referred to as projection angles α, the output signals of the detector elements of the detector system 9 for the corresponding projections are supplied to the electronic calculating unit 13 that uses these output signals to calculate the attenuation values of the slice of the patient 11 covered by the X-ray beam 8 and belonging to the individual detector elements and, thus, channel angles β.

Figure 3:
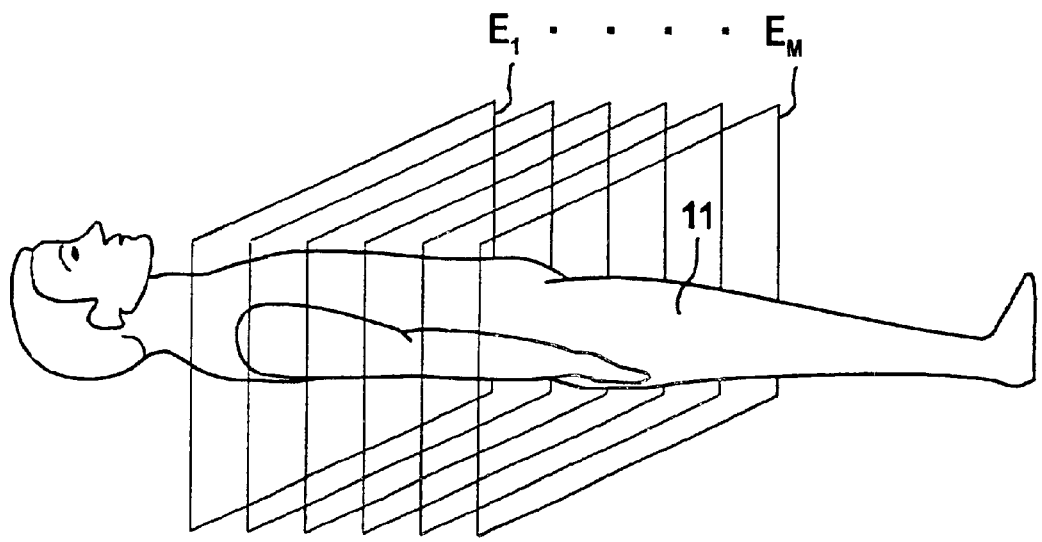
FIG. 3 is a diagram illustrating the acquisition of the measured data to be processed according to the sinventive method.

Since the support plate 2 is displaceable in the direction of the system axis z, a volume of the patient 11 can be scanned so that, as shown in FIG. 3, a number of parallel slices $E_1$ through $E_M$, that preferably adjoin one another, are successively scanned (referred to as a sequence scan), sets of attenuation values corresponding to the scanned, planar slices are supplied to the electronic calculating unit 13. Using these values, the electronic calculating unit 13 determines tomograms on the basis of known reconstruction algorithms. The effective slice thickness of the reconstructed tomograms corresponds to the collimated slice thickness set in the scanning of the examination subject, and the z-positions of the slices imaged in the reconstructed tomograms correspond to the z-positions of the support plate 2 while scanning the examination subject 11.

Ultimately, thus, attenuation values $S(\alpha, \beta, z_j)$ of the scanned slices are available, whereby β is the fan angle of the respective attenuation value, α is the projection angle of the respective attenuation value, $z_j$ is the position on the system axis (z-position) belonging to the respective attenuation value.

If the CT apparatus according to FIGS. 1 and 2 were operated so that the tomograms are not directly calculated in accordance with the initially described disadvantages would be present.

The operation of the CT apparatus on the basis of the inventive method offers additional degrees of freedom that allow the aforementioned disadvantages of the known methods to be avoided or at least reduced, namely by determining resultant attenuation values $\hat{S}(\alpha, \beta, z_j)$ for the table position $Z_r$ from the attenuation values $S(\alpha, \beta, z_j)$.

In the superimposition of the attenuation values of individual tomograms registered in the scanning of a number of different z-positions, the additional parameters of number of slices $N_s$ involved in the superimposition, distance between two successive slices involved in the superimposition in z-direction, $z_{j+1}, -z_j$ and degree of the contribution $g(z_r-z_j)$ of the attenuation values of the $j^{th}$ slice involved in the superimposition arise for the resultant attenuation values. The general case of the inventive method is established by $$\hat{S}(\alpha, \beta, z_r) = \frac{\sum_{j=1}^{N_S} g(z_r - z_j) S(\alpha, \beta, z_j)}{\sum_{j=1}^{N_S} g(z_r - z_j)} \quad (1)$$

with $\alpha=0, \ldots 2\pi$ and $\beta=\beta_1, \ldots \beta_N$. $\Delta z_j=z_{j+1}-z_j$ will usually be constant, the distance between two neighboring tomograms is the same. This, however, is not a necessary condition for the functionability of the inventive method.

Figure 4:
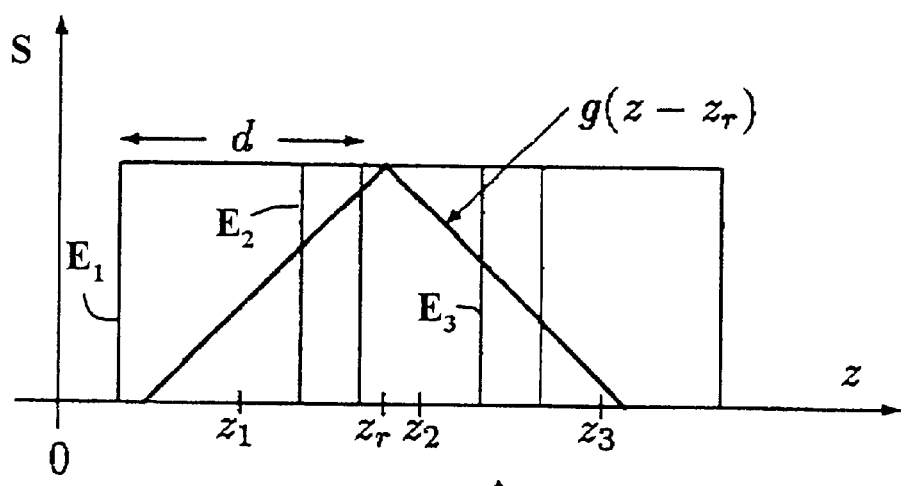
FIG. 4 is a diagram illustrating the functioning of the inventive method.

The significance of Equation (1) is additionally illustrated by FIG. 4, which shows an example with $N_s=3$. The scanning of the individual slices $E_1$ through $E_3$ with the collimated slice thickness d ensued with a distance of $\Delta z=0.75d$ between neighboring slices. As an example, $$g(z) = \begin{cases} 1 - \frac{3|z|}{4\Delta z} & |z| \le 4/3\Delta z \\ 0 & \text{otherwise} \end{cases} \quad (2)$$

was selected for $g(z)$.

The inventive method defined by Equation (1) offers a number of advantages over known methods:

Since the calculation operates on attenuation values, only as many tomograms as required are calculated. This reduces the calculating time for the reconstruction of a resultant tomogram by the factor $N_s$ compared to a superimposition of tomograms.

A further time advantage arises in that, due to the large effective slice thicknesses that the resultant tomograms can comprise in the inventive method, noticeably fewer tomograms are required for covering a specific volume with tomograms compared to the traditional procedure given sequence exposures with low collimated slice thicknesses. The diagnosis by the physician thus takes correspondingly less time. The documentation outlay is also reduced. The gains that can be achieved here are dependent on the collimated slice thickness that has been set as well as on the distance in the z-direction between the individual slices, and on the selected image reconstruction increment.

In addition to the advantages of the conventional procedure in sequence exposures, the effective slice thickness of the tomograms also can be selected in the inventive method in addition to the z-position and the z-spacing of the tomograms from one another.

The inventive method can be implemented in various embodiments with specific properties, with the specific properties, which lead to different resultant tomograms, being respectively dependent on the combination of $N_s$, $z_{j+1}-z_j$ and $g(z)$ being employed.

According to a first embodiment of the inventive method, for example, a suitable selection of $\Delta z$, $g(z)$ and of $N_s$ yields the possibility of varying the noise amplitude of a resultant tomogram independently of the noise amplitude that a tomogram reconstructed out of unmodified attenuation values would exhibit. When, for example, one selects $\Delta z=d$ and $$g(z) = \begin{cases} 1 & |z| \le 0,5(N_S-2)\Delta z \\ 1 - \frac{|z| - 0,5(N_S-2)\Delta z}{\Delta z} & \text{for } 0,5(N_S-2)\Delta z < |z| \le 0,5N_S\Delta z \\ 0 & \text{otherwise} \end{cases} \quad (3)$$

then one obtains $$\hat{S}(\alpha, \beta, z_r) = \frac{1}{N_S - 1} \sum_{j=1}^{N_S} g(z_r - z_j) S(\alpha, \beta, z_j). \quad (4)$$

from Equation (1).

A resultant tomogram reconstructed on the basis of these resultant attenuation values exhibits a noise amplitude of approximately $$\sigma = \sqrt{\frac{1}{N_S - 1}} \sigma_d \quad (5)$$

where $\sigma_d$ is the noise amplitude of an individual tomogram with the collimated slice thickness that was registered during the course of a sequence. The resulting slice thickness of the resultant tomogram is $$d_{eff}=(N_s-1)d \quad (6).$$

According to a second embodiment of the inventive method, a suitable selection of $\Delta z_j$, $N_s$ and $g(z)$ yields the possibility of varying the half-width value of the slice sensitivity profile, i.e. the effective layer thickness, of the resultant tomogram independently of the collimated slice thickness. When, for example, one selects $N_s=4$, $\Delta z_j=\Delta z=d/2$ and $$g(z) = \begin{cases} 1 + w - (1 + 1.5w)\frac{|z|}{\Delta z} & |z| \le \Delta z \\ \frac{w|z|}{2\Delta z} - w & \text{for } \Delta z < |z| \le 2\Delta z \\ 0 & \text{otherwise} \end{cases} \quad (7)$$

then this leads to an effective slice thickness $$d_{eff}=0.5d \quad (8)$$

and to a noise amplitude of $$\sigma = \sqrt{\frac{41}{64}} \sigma_d \quad (9)$$

given a reconstruction of resultant tomograms at the z-positions $Z_k=z_1+(k+0.5)\Delta z$ with the value w=0.25.

For setting the effective slice thickness $d_{eff}$ of the resultant tomogram, a further embodiment of the inventive method provides that the following is valid for $\Delta z$ and $g(z)$:

$\Delta z=d$ and $$g(z) = \begin{cases} 1 & |z| \leq 0,5(N_S - 2)\Delta z \\ 1 - \dfrac{|z| - 0,5(N_S - 2)\Delta z}{\Delta z} & \text{for } 0,5(N_S - 2)\Delta z < |z| \leq 0,5 N_S \Delta s \\ 0 & \text{otherwise} \end{cases}$$

and with $N_s$ is selected according to the equation $$\sigma = \sqrt{\dfrac{1}{N_S - 1}} \sigma_d$$

for achieving a desired noise amplitude a of the resultant tomogram.

According to another version of the inventive method, the reduction of partial volume artifacts is also possible when $$\Delta z = d$$

$$g(z) = \begin{cases} 1 & |z| \leq 0,5(N_S - 2)\Delta z \\ 1 - \dfrac{|z| - 0,5(N_S - 2)\Delta z}{\Delta z} & \text{for } 0,5(N_S - 2)\Delta z < |z| \leq 0,5 N_S \Delta z \\ 0 & \text{otherwise} \end{cases}$$

and $$N_s > 4$$

are valid for $\Delta z$, g(z) and $N_s$.

This embodiment of the inventive method unites the low artifact amplitude of a scan having a small collimated slice thickness d with the low noise amplitude of a scan having a large collimated slice thickness d, which represents a significant clear improvement over known methods.

Regardless of the embodiment of the inventive method employed for the reconstruction of the resultant tomogram, a reduction of the calculating time compared to known methods is achieved since only a single tomogram, namely the resultant tomogram, has to be calculated instead of $N_s$ tomograms, whereby the calculating time required for the determination of the resultant attenuation values can normally be neglected.

With the inventive method, moreover, a reduction of the radiation stress on the examination subject is always achieved as a result of the fact that, with the inventive method, resultant tomograms with parameters that would require the implementation of a further scan using known methods can be reconstructed on the basis of a single scan.

In the exemplary embodiment, the relative motion between the measuring unit 5 and the support plate 2 is generated by displacing the support place 2. It is also possible in the inventive method, however, to leave the support plate 2 stationary and to displace the measuring unit 5 instead. There is also the possibility within the scope of the invention of generating the necessary relative motion by displacing both the measuring unit 5 and the support plate 2.

An electronic control unit 14 serving essentially for the control of the CT apparatus and an electronic calculating unit 13 serving essentially for image generation, are provided in the described exemplary embodiment. Instead, a single control and calculating unit can be used that assumes both the tasks of control and of image generation.

The above-described CT apparatus has a detector system with a single line of detector elements. Within the scope of the invention, a number of lines of detector elements, for example 16 lines of 800 detector elements each, or matrix-like arrangements of detector systems comprising detector elements, can be used instead. If so, a pyramidal or conical X-ray beam adapted to the arrangement of the detector elements will emanate from the X-ray source, rather than a fan-shaped X-ray beam.

The invention has been described above with reference to the example of a CT apparatus with a vertically oriented gantry wherein the measurement plane and the z-direction are perpendicular to one another. It is also possible to employ the inventive method for data registered with a gantry inclined by the angle γ relative to the vertical. In this case, calculations are to be carried out with the numerical values Δz/cosγ instead of the numerical values Δz.

The invention has been described above with reference to the example of a CT apparatus of the third generation, wherein the X-ray source and the detector system rotate in common. However, the inventive method also can be used in a CT apparatus of the fourth generation, wherein a rotating X-ray source collaborates with a stationary ring of detector elements.

The inventive method can also be employed in a CT apparatus of the fifth generation, wherein the X-rays emanate not only from one focus but from a number of foci of one or more X-ray sources displaced around the system axis.

The above-described exemplary embodiments relate to the medical application of the inventive method. The invention, however, also can be applied beyond medicine, for example in baggage inspection or in the inspection of materials.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating a resultant tomogram from a plurality of tomograms registered with a computed tomography apparatus comprising scanning slices of an examination subject that have different attenuation values acquired during the scan at fixed positions on a system axis, superimposing the attenuation values acquired when scanning the individual slices to form resulting attenuation values, and reconstructing a resultant tomogram from the resulting attenuation values.

2. A method according to claim 1, wherein the computed tomography apparatus has a system axis, and wherein the superimposition of the attenuation values acquired in the scanning of the individual slices to form resulting attenuation values ensues according to $$\tilde{S}(\alpha, \beta, z_r) = \frac{\sum_{j=1}^{N_S} g(z_r - z_j) S(\alpha, \beta, z_j)}{\sum_{j=1}^{N_S} g(z_r - z_j)}$$

wherein $S(\alpha, \beta, z_j)$ are the attenuation values of the several slices, and $\beta$ is a fan angle of the respective attenuation value, $\alpha$ is a projection angle of the respective attenuation value, $z_j$ is a position on said system axis belonging to the respective attenuation value, wherein $\tilde{S}(\alpha, \beta, z_r)$ is the result of the superimposition (resulting attenuation values) of the attenuation values of the several slices, and $Z_r$ is the position on the system axis belonging to the resulting attenuation values, and wherein $N_s$ is a plurality of slices involved in the superimposition, $g(z_r-z_j)$ is a strength of the contribution of the $j^{th}$ slice to the result of the superimposition.

3. A method according to claim 2, comprising modifying a noise amplitude of the resultant tomogram by modifying at least one of the parameters $\Delta z$, g(z) and $N_s$, whereby $\Delta z$ is the distance between two successive slices involved in the superimposition.

4. A method according to claim 3, wherein $$\Delta z = d$$

and $$g(z) = \begin{cases} 1 & |z| \leq 0,5(N_S - 2)\Delta z \\ 1 - \frac{|z| - 0,5(N_S - 2)\Delta z}{\Delta z} & \text{for } 0,5(N_S - 2)\Delta z < |z| \leq 0,5 N_S \Delta z \\ 0 & \text{otherwise} \end{cases}$$

are valid for the parameters $\Delta z$ and g(z) and that the parameter $N_s$ is selected according to $$\sigma = \sqrt{\frac{1}{N_d - 1}} \sigma_d$$

for achieving a desired noise amplitude of the resultant tomogram, whereby $\sigma$ is a noise amplitude of the resultant tomogram, and $\sigma_d$ is a noise amplitude of an individual tomogram having the collimated slice thickness d.

5. A method according to claim 2, comprising influencing an effective slice thickness of the resultant tomogram by modifying at least one of $\Delta z$, g(z) and $N_s$, wherein $\Delta z$ is a distance between two successive slices involved in the superimposition.

6. A method according to claim 5, wherein $$\Delta z = d$$

and $$g(z) = \begin{cases} 1 & |z| \leq 0,5(N_S - 2)\Delta z \\ 1 - \frac{|z| - 0,5(N_S - 2)\Delta z}{\Delta z} & \text{for } 0,5(N_S - 2)\Delta z < |z| \leq 0,5 N_S \Delta z \\ 0 & \text{otherwise} \end{cases}$$

are valid for the parameters $\Delta z$ and g(z) and that the parameter $N_s$ is selected according to the equation $$d_{\textit{eff}} = (N_s - 1)d$$

wherein $d_{\textit{eff}}$ is an effective slice thickness of the resultant tomogram, and d is a collimated slice thickness of an individual tomogram.

7. A method according to claim 2, wherein $\Delta z$ is a distance between two successive slices involved in the superimposition, and wherein $$\Delta z = d$$

and $$g(z) = \begin{cases} 1 & |z| \leq 0,5(N_S - 2)\Delta z \\ 1 - \frac{|z| - 0,5(N_S - 2)\Delta z}{\Delta z} & \text{for } 0,5(N_S - 2)\Delta z < |z| \leq 0,5 N_S \Delta z \\ 0 & \text{otherwise} \end{cases}$$

and $$N_s > 4$$

are valid for the parameters $\Delta z$, g(z) and $N_s$.

* * * * *